United States Patent
Lee et al.

(10) Patent No.: US 7,037,425 B2
(45) Date of Patent: May 2, 2006

(54) MESOPOROUS MEMBRANE COLLECTOR AND SEPARATOR FOR AIRBORNE PATHOGEN DETECTION

(75) Inventors: Gil U. Lee, West Lafayette, IN (US); Sang Won Lee, Burbank, CA (US)

(73) Assignee: Purdue Research Foundation, West Lafayette, IN (US)

( * ) Notice: Subject to any disclaimer, the term of this patent is extended or adjusted under 35 U.S.C. 154(b) by 297 days.

(21) Appl. No.: 10/313,376

(22) Filed: Dec. 6, 2002

(65) Prior Publication Data

US 2003/0222012 A1 Dec. 4, 2003

Related U.S. Application Data

(60) Provisional application No. 60/388,239, filed on Jun. 13, 2002, and provisional application No. 60/340,012, filed on Dec. 6, 2001.

(51) Int. Cl.
*B01D 63/00* (2006.01)

(52) U.S. Cl. ............... 210/321.75; 210/321.6; 210/500.25; 210/500.26; 210/490; 210/500.27; 422/99; 422/101; 422/57; 422/58; 422/186.1; 436/518

(58) Field of Classification Search ........... 210/321.6, 210/321.75, 500.25, 500.26, 500.27, 490, 210/645; 427/376.62; 422/99, 100, 101, 57, 422/58, 186.1; 436/518; 55/523, 524
See application file for complete search history.

(56) References Cited

U.S. PATENT DOCUMENTS

| 4,160,645 | A | | 7/1979 | Ullman |
| 4,687,551 | A | | 8/1987 | Furneaux et al. |
| 5,250,184 | A | | 10/1993 | Maier |
| 5,378,440 | A | * | 1/1995 | Herbst et al. ............... 423/210 |
| 5,468,847 | A | | 11/1995 | Heilmann et al. |
| 5,645,891 | A | * | 7/1997 | Liu et al. ................. 427/376.2 |
| 5,789,024 | A | | 8/1998 | Levy et al. |
| 5,807,758 | A | | 9/1998 | Lee et al. |
| 6,180,418 | B1 | | 1/2001 | Lee |
| 6,676,904 | B1 | | 1/2004 | Lee et al. |
| 6,719,147 | B1 | * | 4/2004 | Strano et al. ............... 210/490 |

FOREIGN PATENT DOCUMENTS

WO    WO 03/049840    6/2003

OTHER PUBLICATIONS

Beamson et al., "High Resolution XPS of Organic Polymers," *The Scienta ESCA300 Data Base*, Wiley, New York, 1992; cover page, title page and table of contents only.

(Continued)

*Primary Examiner*—Ana Fortuna
(74) *Attorney, Agent, or Firm*—Woodard, Emhardt, Moriarty, McNett & Henry LLP

(57) ABSTRACT

A process and apparatus for the collection of biological materials from air. Collection and separation devices utilize a novel membrane structure formed from a functionalized inorganic mesoporous membrane supported by porous substrate.

12 Claims, 16 Drawing Sheets

OTHER PUBLICATIONS

Briggs et al., *Practical Surface Analysis*, $2^{nd}$ ed., vol. I, Briggs et al., eds., New York, 1996; cover page, title page and table of contents only.

Crank, *The Mathematics of Diffusion*, Oxford Press, 1956; cover page, title page and table of contents only.

Dalvie et al., "Transport studies with porous alumina membranes" *Journal of Membrane Science*, 1992; 71:247–255.

Finnie et al., "Formation and Patterning of Self–Assembled Monolayers Derived from Long–Chain Organosilicon Amphiphiles and Their Use as Templates in Materials Microfabrication" *Langmuir*, 2000; 16(17):6968–6976.

Grabar et al., "Preparation and Characterization of Au Collolid Monolayers," *Anal. Chem.*, 1995;67(4):735–43.

Green, et al., "Effect of Mechanical Contact on the Molecular Recognition of Biomolecules," *Langmuir*, 1999; 15:238–43.

Gölander et al., "ESCA Studies of the Adsorption of Polyethyleneimine and Glutaraldehyde–Reacted Polyethyleneimine on Polyethylene and Mica Surfaces" *J. Colloid Interface Science*, 1987; 119(1):38–48.

Jeon et al., "Structure and Stability of Patterned Self–Assembled Films of Octadecyltrichlorosilane Formed by Contact Printing," *Langmuir*, 1997; 13(13):3382–91.

Kiss et al., "Surface grafting of polyethyleneoxide optimized by means of ESCA" *Prog. Colloid Polym. Sci.*, 1997; 74:113–119.

Matsumoto et al., "Association State, Overall Structure, and Surface Roughness of Native Ovalbumin Molecules in Aqueous Solutions at Variuos Ionic Concentrations" *Journal of Colloid and Interface Science*, 1993; 160:105–09.

Matsumoto et al., "Effect of pH on colloid properties of native ovalbumin aqueous system," *Colloid and Polymer Science*, 270:687–93.

Metzger et al., "Development and Characterization of Surface Chemistries for Microfabricated biosensors," *J. Vac. Sci. Technol. A.*, 1999; 17(5):2623–2628.

Mucic, et al., "DNA–Directed Synthesis of Binary Nanoparticle Network Materials," *J. Am. Chem. Soc.*, 1998; 120:12674–5.

Storhoff et al., "One–Pot Colorimetric Differentiation of Polynucleotides with Single Base Imperfections Using Gold Nanoparticle Probes," *J. Am. Chem. Soc.*,, 1998; 120(9):1959–64.

* cited by examiner

MESOPOROUS MEMBRANE COLLECTOR AND SEPARATOR FOR AIRBORNE PATHOGEN DETECTION

This application claims the benefit of U.S. Provisional Application Ser. No. 60/388,239, filed Jun. 13, 2002, and U.S. Provisional Application Ser. No. 60/340,012, filed Dec. 6, 2001, which are incorporated herein by reference in their entireties.

STATEMENT OF GOVERNMENT RIGHTS

This invention was made with government support under a grant from the Department of Navy, Grant No. NAVSEA/ NSWC CRANE N000164-00-C-0047. The U.S. Government has certain rights in this invention.

BACKGROUND OF THE INVENTION

As a result of elevated public concern about the safety of our water and food supplies and the ability of infectious diseases to rapidly spread through our globalized economies, pathogen detection is becoming increasingly important. Currently, the identification of most pathogens is achieved through the collection of a liquid sample. Common detection techniques involve either selectively culturing an organism or specifically identifying a marker of an organism. These techniques typically are not sufficiently sensitive to detect many pathogens that may be present at infectious levels. It may take hours (or days) to obtain the desired information. In addition, these techniques are often prohibitively expensive to implement on a continuous basis.

It may be more convenient, or even necessary, to analyze an air sample rather than a liquid sample. Environmental monitoring of the air is typically conducted in one of two ways, depending on whether the analyte is a biological or nonbiological analyte. For a nonbiological analyte, such as a radioisotope or a material such as asbestos, the sample is collected on a membrane, and the collected sample material is analyzed using the appropriate detection technology.

Membranes, however, have not been as useful in detecting airborne biological organisms. The continuous flow of dry air over a membrane desiccates the organism and makes it difficult to detect the organism using cell culture or other bioanalytical techniques. In addition, a major drawback in using membrane is fouling due to the protein adsorbing on the membrane surface. Instead, biological organisms typically are collected from the air using techniques such as the wetted wall cyclone separator. The airborne pathogens are collected by taking advantage of their inertia when as stream of air is forced to spin in a cyclonic manner, then entrained in a fluid for subsequent identification using flow cytometry, solid-phase immunoassay or cell culture. This method of detection is very expensive to operate on a continuous basis as it consumes tens of milliliters of reagent a minute to identify a pathogen at relevant concentrations.

A system that allows for more economical and effective detection of airborne pathogens is needed.

SUMMARY OF THE INVENTION

The invention provides a device and process that allow for the collection of biological materials from a gaseous environment, extraction of the collected materials, separation, and presentation of these materials for analysis using bioanalytical techniques. Collection, extraction and/or separation of the biological materials is accomplished using one or more mesoporous membranes. The mesoporous membranes preferably have specific physical and/or chemical properties that enhance their function. The membranes are robust and can be continuously reused during this process. This system will quickly detect pathogens at low concentrations using minimal amounts of reagent.

In one aspect, the invention provides a novel membrane structure for collection or separation of a biological material present in a fluid sample. The membrane structure includes a mesoporous membrane and a porous substrate. The mesoporous membrane is preferably fabricated from an inorganic material having high elastic modulus. The pores in the mesoporous membrane are typically nanometer size in scale, whereas the pores in the porous substrate are typically 1 mm or more in diameter. The porous substrate is disposed adjacent the support surface of the mesoporous membrane such that, when in use, fluid enters the membrane structure at the active surface, passes through the mesoporous membrane, and exits the membrane structure without being obstructed by the porous substrate.

The active surface of the mesoporous membrane is preferably derivatized with an organic material, preferably in the form of a hydrophilic polymer monolayer, to facilitate removal of sample components from the surface and/or to prevent adhesion of sample components to the membrane surface.

In another aspect, the invention provides a collector for collecting a biological material present in gaseous sample. The collector includes a collection portion that includes a membrane structure according to the invention and at least one inlet and outlet that provide a path for the flow of a gas through the membrane structure. Biological material is collected on the active surface of the mesoporous membrane.

Optionally, the collector includes an extraction portion in fluid communication with the membrane structure. An actuator can also be included to move the membrane structure from the collection portion to the extraction portion of the collector.

In another aspect, the invention provides a separator for separating biological materials present in a liquid sample. The separator includes at least one membrane structure according to the invention and at least one inlet and outlet that provide a path for the flow of a liquid through the membrane structure. A plurality of membrane structures can be used in series, each with a smaller pore size as the liquid sample moves downstream for further separation of sample components.

In another aspect, the invention provides a system for detecting a biological material present in a gaseous sample. The system includes a collector and optional separator according to the invention, and optionally a detector. The separator is in fluid communication with the collector. The collector is configured to provide a liquid sample comprising the extracted biological materials to the separator, and the separator is operable to receive the liquid sample from the collector and separate the biological materials in the liquid sample. The detector is configured to receive the separated biological materials from the separator (or the collector, if no separator is used), and is operable to detect and analyze the separated biological materials.

In yet another aspect, the invention provides a method for collecting an airborne biological material. A stream of gas is directed through the membrane structure of a collector according to the invention, such that the gas stream enters the membrane structure at the active surface, passes through the mesoporous membrane, and exits the membrane structure without being obstructed by the porous substrate. A sample is collected from the gas stream on the active surface of the mesoporous membrane, then removed therefrom. Removing the sample from the active surface of the mesoporous membrane is accomplished in the presence of a liquid, which can be aqueous or organic depending on the nature of the sample and the membrane chemistry. The biological material in the sample is typically detected and analyzed after removal from the membrane. When the collector includes both a collection portion and an extraction portion, the method further includes transferring a collected sample from the collection portion to the extraction portion prior to removing the sample from the mesoporous membrane.

Advantageously, because the membrane surface modifications prevent fouling of the membrane during use, the membrane structure is reusable, and sample collection can be performed continuously.

In another aspect, the invention provides a method for separating biological materials in a liquid sample. A liquid sample is contacted with a membrane structure of a separator according to the invention, such that the liquid enters the membrane structure at the active surface, passes through the mesoporous membrane, and exits the membrane structure without being obstructed by the porous substrate. At least one sample component does not pass through the mesoporous membrane, resulting in separation of the biological materials. Multiple separation membranes can be used in series to effect further separation of the sample components. The biological material in the sample is typically detected and analyzed after separation.

Advantageously, because the membrane surface modifications prevent fouling of the membrane during use, the membrane structure is reusable, and separation of sample components can be performed continuously.

Collection, separation and detection of biological materials can be achieved using an integrated system according to the invention. The liquid sample removed from the surface of the collector membrane is transferred to the separator, and after separation the biological material is transferred to the detector. As noted, the use of the novel membrane structures of the invention allow the system to be operated continuously.

In another aspect, the invention includes method for modifying the mesoporous membrane to facilitate removal of a biological sample therefrom and/or inhibit adhesion of sample components thereto. Various embodiments of the method of making the modified membranes of the invention are illustrated in FIG. 6.

DETAILED DESCRIPTION OF ILLUSTRATIVE EMBODIMENTS

Figure 1:
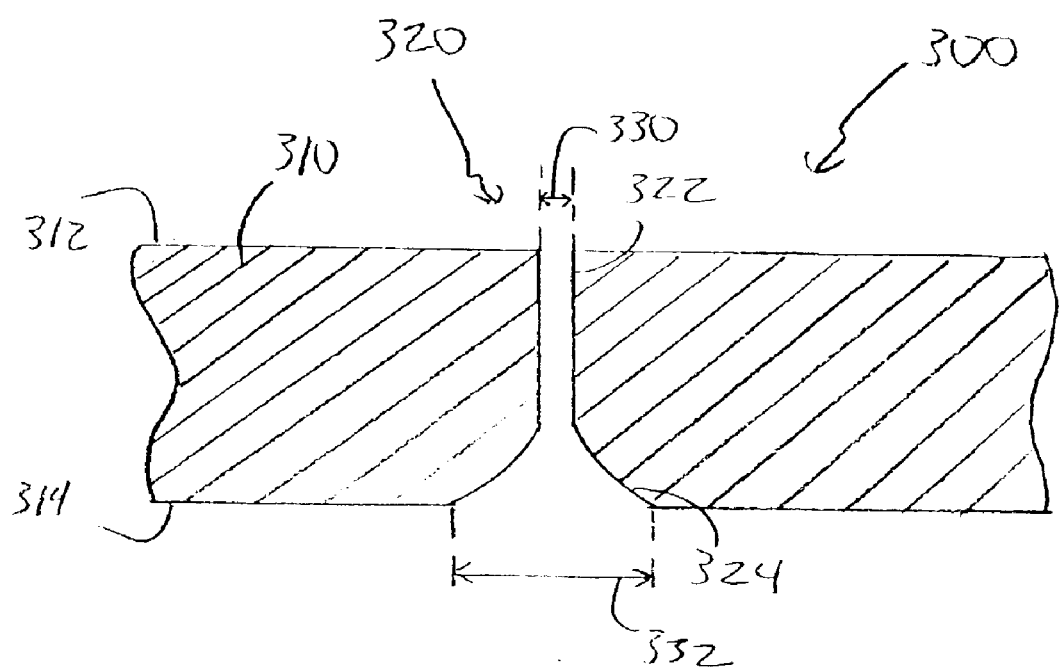
FIG. 1 is a diagrammatic cross-sectional view of a pore of an unmodified mesoporous membrane according to the present invention.

Conventional membrane-based collection and separation systems for airborne materials, such as those utilizing a polymeric membrane supported by a nitrocellulose layer and a glass frit, produce an unacceptably large drag for high volume air sampling due to the use of multiple membranes, tortuous flow paths, and hydrodynamically inefficient mechanical supports.

The present invention provides a robust mesoporous membrane which, when supported by a porous substrate, is suitable for use in a collector or separator device as described herein. A "mesoporous" membrane, as the term is used herein, includes pores having a pore diameter in a range of about 1 nm to about 1000 nm. Drag and the consumption of reagents are minimized during use of the membrane of the invention because sample flow is not impeded by the support material as in conventional filtration systems, such as those that use glass frits, paper, and the like to support the ultrafiltration membrane. The mesoporous membrane is preferably modified to inhibit adhesion of biological molecules, particularly proteins. Surface modifications of the membrane can be hydrophilic or hydrophobic, although hydrophilic polymer modifications are preferred.

The collector device has a body and a membrane structure located within the body. The membrane structure may include a porous substrate and a mesoporous membrane on the porous substrate. Pore size of the mesoporous membrane is selected to be permeable to air but to occlude biological materials of interest. In the collector device, air is pumped through the mesoporous membrane. Some airborne biological materials may be collected on a surface of the mesoporous membrane as air containing the biological materials passes through the membrane structure. The mesoporous membrane is then wetted, and the collected biological materials are extracted or otherwise removed from the active surface of the mesoporous membrane as a liquid sample using techniques known in the art. The extracted materials can be transferred to a detector and analyzed directly or transferred to a separator device for further processing.

The separator device has a body and at least a first membrane structure within the body. The first membrane structure is similar to the membrane structure of the collector, except that it typically differs in pore size. Pore sizes are selected with molecular weight cutoffs to isolate the biological material of interest. If two or more mesoporous membranes are used, they are arranged in series to process a liquid sample by size exclusion. Biological materials that are not isolated by the first membrane structure may pass through the first membrane structure and contact a second membrane structure that includes a mesoporous membrane having a different pore size than the mesoporous membrane of the first membrane structure. The second membrane structure may then isolate biological materials having a selected molecular weight and transfer such biological materials to a detector for detection and analysis. The separator may include any suitable number of membrane structures for isolating biological materials of varying molecular weights.

The collector device and the separator device can, if desired, be operated as an integrated unit. However it should be understood that the collector and separator devices may also be used independently of one another. For example, if an airborne sample is relatively clean, a separator device may not be needed prior to identification and characterization of biological material collected with the collector device. Likewise, the separator device can be used without the collector device to process a liquid sample prepared or obtained by any convenient means.

The biological material(s) collected and/or separated using the collector or separator device of the invention are optionally detected using a detector that allows identification, characterization, analysis and/or quantification of the biological material. Detection can be accomplished by any convenient means, such as spectroscopically, for example using mass spectroscopy, or biochemically, for example by using DNA hybridization or immunoassay. Typically, the nature of the marker to be detected determines the nature of the detector. For example, if a gene is to be detected, a hybridization assay may be used in the detector; if a toxin is to be detected, mass spectrometry may be the better choice; and if a whole organism is to be detected, an immunoassay utilizing an antibody with specificity toward that organism may be selected.

Mesoporous Membrane

The mesoporous membrane is preferably fabricated from an inorganic material and is characterized by a high elastic modulus (several times higher than polymeric membranes). Inorganic membranes typically have a narrow pore distribution, a high pore density, and thinness. High quality anodisc alumina membranes are now available and are especially useful. Silicon is also expected to be a suitable material for the mesoporous membrane. Alumina membranes made by anodic oxidation permit the perpendicular flow of fluid (liquid or gas) through the membrane because they contain straight (i.e., nontortuous; see FIG. 1) circular pores with a very uniform pore size. The thickness of such membranes is a function of the anodization time and varies between a few nanometers to up to hundreds of micrometers. These membranes exhibit many advantages over polymeric membranes including 1) high flow rates, 2) transparent when wet, enabling easy for light microscope evaluation of cell growth, 3) no background stain, and 4) uniform pore size and high distribution.

For example, FIG. 1 is a diagrammatic cross-sectional view of a pore 320 of an unmodified mesoporous membrane 300. As depicted, the mesoporous membrane 300 includes a membrane body 310 having an active surface 312 and a support surface 314. The pore 320 begins at the active surface 312 and traverses the membrane body 310 to the support surface 314 in a direction generally orthogonal to the active surface 312.

The pore 320 includes a first portion 322 proximate the active surface 312 and a second portion 324 proximate the support surface 314. The first portion 322 includes a diameter 330, and the second portion 324 includes a diameter 332. In general, diameter 332 is greater than diameter 330 such that the pore 320 increases in diameter proximate the support surface 314. Although depicted as having a variable diameter, the pore 320 may include a uniform diameter.

The mesoporous membrane contains pores having a nanometer-scale pore diameter, preferably between about 1 nm to about 1000 nm. The pore diameter is determined by the applied voltage. The pore size is selected to achieve the desired function. Circular pores are preferred, but the invention is not limited by or to any particular pore shape.

In a collector device, a larger pore size (e.g. 200 nm or greater) is typically selected for the mesoporous collection membrane to allow rapid air flow through the membrane. Airborne biological materials are typically in the form of a micron-scale aerosol, therefore these materials would be expected to remain trapped on the surface of the mesoporous membrane regardless of pore size. Material extracted from the collector membrane is processed to break down the aerosol into much smaller components.

In a separator device, a smaller pore size (e.g., 200 nm or smaller) is typically selected for the mesoporous separation membrane(s) to achieve the desired separation of biological materials based on particle size. For example, the first separation membrane in a series could contain 200 nm pores, the second 10 nm pores, and the third 2 nm pores. Typically the pores are open (unfilled), but they can optionally be partially or completely filled with a sieving material such as a polymeric matrix (e.g., agarose or polyacrylainde). In yet another embodiment, a very thin sieving layer can be applied to the active surface of the mesoporous membrane, or the support surface of the mesoporous membrane, such that it is interposed between the mesoporous membrane and the porous support.

The pores are distributed within the membrane at a density of about $10^7$ to about $10^{12}$ pores per m$^2$ or even higher, depending on pore size. Generally, a higher pore density may be preferred.

As detailed below, because of their high elastic modulus, membranes fabricated from inorganic materials do not need much support; typically a porous substrate having relatively large pores (typically 3–5 mm) compared to the pore size of the membrane will provide adequate support under normal operating pressures. Also, as noted previously, the flow of air or liquid through the membrane structure of the invention is not impeded by the porous substrate.

Membrane Surface Modification

The inorganic membrane used in the collector and/or separator devices may be chemically or enzymatically modified to yield a hybrid inorganic/organic mesoporous membrane (referred to herein as a "functionalized" or "modified" mesoporous membrane) that enables efficient, repeated extraction of biological material such as protein, virus and bacteria particles therefrom. In air, the primary source of adhesion of biological organisms to the membrane is capillary forces, which arise from the wetting of the membrane and the analyte due to humidity. In water, the primary source of adhesion of biological organisms to membranes is multivalent interaction (i.e., hydrogen bonding, salt bridges, and van der Waals interactions) between macromolecules on the organisms and the surface. Minimization of adhesion of biological organisms to the mesoporous membrane is desirable because it facilitates extraction and subsequent analysis and identification of the biological material and makes the membrane reusable, thus minimizing the cost of the analysis.

The surface of the membrane is preferably modified by grafting biocompatible polymer chains on the membrane surface to prevent non-specific protein adsorption and cell adhesion, thereby preventing membrane fouling, a major problem with polymeric membranes. This process can render the surface hydrophilic (such as by using a water-soluble polymer) or hydrophobic (such as by using a hydrophobic polymer). The membrane surface can be modified, for example, with various molecules such as albumin, heparin, polyalkylene glycols such as poly(ethylene glycol) (PEG), dextrans, starches such as cellulose, self-assembled monolayers (SAMs) and phospholipids.

Hydrophilic polymer modifications to the active surface of the membrane are preferred, as they are effective in reducing multivalent interactions between macromolecules on the extracellular surface of the organisms, and the surface of the mesoporous membrane(s) used in a separator (e.g., separator 200 of FIG. 3) to minimize fouling of the membranes. To reduce these interactions, the mesoporous membrane surface can be functionalized with the appropriate polymeric or monolayer chemistries. PEG is preferred due to its hydrated, neutral, highly mobile, and flexible chains. Densely grafted hydrophilic polymers, such as polyethylene glycol (PEG) are known to minimize adhesion if they have a low probability of interacting with the organism.

Alternatively, capillary forces within a membrane structure can be reduced if the surface of the membrane structure is made hydrophobic. Examples of surface chemistries for making membranes hydrophobic include silanes or alkane thiol monolayers. We have developed techniques for depositing monolayers of silane molecules (e.g., octadecyltrichlorisilane (OTS), octadecyldimethylmethoxysilane, or their fluorinated analogs) on the membrane. Likewise, saturated mercaptoalkane (or their fluorinated analogs) can be deposited on 5–50 nm thick Au films on the membrane surface. Both techniques provide non-stick surfaces from which aerosol samples can be easily extracted with a high degree of efficiency. When hydrophobic modifications are employed, it may be useful to use an organic solvent such as acetonitrile, acetone, dimethylsulfoxide, dichloromethane or chloroform to extract the biological materials from the membrane surface.

Porous Substrate Support

The nanoporous membrane is supported by a porous substrate, typically planar, wherein the substrate pores are millimeter-scale in size (e.g., 1, 5, 10 mm). The supporting substrate can be fabricated, for example, from glass, silicon, metal, plastic or any other material that is reasonably strong and can be formed with reasonable tolerances. Gas (in the case of a collector membrane) and/or liquid (in the case of a separator membrane(s)) readily passes through the nm-scale pores in the nanoporous membrane and is unobstructed by the mm-scale openings of the supporting substrate. That is, the flow of fluid flow through the mesoporous membrane is not impeded by the porous substrate.

The pore size of the support substrate is selected to prevent rupture of the particular nanoporous membrane under the conditions of operation, and varies accordingly with the pore size of the nanoporous membrane and the fluid pressure in the device. A fluid pressure of about 45 to about 100 psi is a typical operating pressure for the device, but operating pressures can extend well below and above that range, depending upon, for example, the nature of the sample, membrane pore size, and the pores size of the support substrate.

An important dimension in the membrane-support layer is the width (diameter) of the opening. If this opening is too large, the membrane will break under normal operating pressures, resulting in the destruction of the device and loss of the sample. On the other hand, if the opening is too small, the device will be highly inefficient.

Table 1 illustrates the effect of pore size on structural integrity of the mesoporous membrane. The measured rupture forces are significantly higher than would have been predicted from calculations of the rupture strength using continuum mechanics and theoretical materials properties of the membranes, indicating that these membranes may be operated at unexpectedly high pressures or using unexpectedly large openings in the supporting layer.

TABLE 1

| | Rupture stress | | | | |
|---|---|---|---|---|---|
| Membrane Pore Size | Rupture Pressure (PSI) | Rupture Pressure ($N/m^2$) | Substrate Pore Size (mm) | Bending Moment at Edge (N) | Rupture Stress (Flexural) ($MN/m^2$) |
| 20 (nm) | 120 | 827371 | 4 | 1.655 | 2758 |
| 100 | 65 | 448159 | 4 | 0.896 | 1494 |
| 200 | 60 | 413685 | 4 | 0.827 | 1379 |

Given the measurements for bending moment and rupture stress reported in Table 1, the optimal mesoporous membrane pore size or rupture pressure can be predicted for different substrate opening sizes.

Advantageously, the collector and separator devices can be constructed to allow the interchangeable use of membranes having any desired pore size, depending upon the application. These elements can, if desired, be fabricated as cartridges for easy insertion and removal. The cartridges may contain one or more membranes and/or one or more membrane/support units.

Biological Materials

The collector and separator devices of the invention are particularly suited to the detection of biological materials, particularly biological organisms such as protozoa, bacteria, viruses, and the like. Biological molecules such as polypeptides, nucleic acids, polysaccharides, lipids, hormones, cofactors and the like an also be detected. The invention is expected to be especially useful to detect biological pathogens.

Extraction and Separation of Biological Materials

Complete extraction of the biological organisms from the mesoporous membrane is desirable, so that the membrane can be used repeatedly. In some cases, it may be possible to use chemically active agents such as surfactants, e.g., sodium dodecylsulfate or Triton-20™. However, surfactants often must be avoided due to incompatibility with the means of detection. Several other extraction processes that could be used include electrostatic and ultrasonic extraction. The mesoporous membrane is wetted, and electrostatic or ultrasonic treatment causes the biological materials to go into solution.

Material extracted from the collector membrane is optionally processed to break down the aerosol into much smaller components. For example, cells may be lysed, and the cell lysate may be separated and analyzed for characteristic components such as proteins or DNA. Immunoassay and DNA hybridization are examples of techniques that can be used to analyze biological materials.

The present invention shall be generally described with reference to FIG. 2. Various embodiments of the present invention shall thereafter be described with reference to FIGS. 3 and 4.

FIG. 2 is a schematic view of one embodiment of a system 10 for detection of airborne biological organisms according to the invention. The system 10 includes a collector/separator component 20. The collector/separator component 20 includes a collector 30 and a separator 40 in fluid communication with the collector 30 via inlet 42. As further described herein, the collector 30 receives air and collects a sample from the air on a membrane structure (not shown). In one embodiment, a pump 50 may be provided to direct air into the collector 30 via inlet 32. In another embodiment, a vacuum 54 may be provided alone or in combination with pump 50. Vacuum 54 is operable to draw air through the collector 30 and out the collector 30 via outlet 36. Any suitable pump and/or vacuum known in the art may be used. Further, any number of pumps and/or vacuums may be used with the present invention.

The collector 30 then extracts the sample from the membrane structure. Various aqueous reagents may be provided to aid in the collection and extraction process via reagent inlet 34. The air is then directed out of the collector 30 through outlet 36.

The extracted sample is then provided to the separator 40 via inlet 42. A pump 56 may be provided to pump the sample into separator 40 via inlet 42. Any suitable pump known in the art may be utilized. The sample is separated, for example by molecular weight, using one or more membrane structures as further described herein. Various aqueous reagents may be provided to aid in the separation process via reagent inlet 44. Waste from the separator 40 is directed out of the collector/separator component 20 through outlet 46.

The system may further include a detector/identifier 60 in fluid communication with the collector/separator component 20. The detector 60 receives the isolated sample via inlet 62. The detector 60 may be any suitable detector known in the art, such as a spectroscopic detector, a biochemical detector, an electrical or electromagnetic detector, or a radioisotope detector. In general, the detector 60 may detect biological materials or their constituent components. The detected materials are optionally transferred to a separate analyzer for identification (not shown).

One illustrative embodiment of the collector 30 of FIG. 2 will be described in greater detail with reference to FIG. 3, which is a schematic view of a collector 100. The collector 100 may be used with the system 10 described above (e.g., as collector 30). The collector 100 includes a body 110 and a membrane structure 120 within the body 110. The body 110 of collector 100 may be made of any suitable materials, e.g., a metal, polymer, or the like.

Further, the body may be any suitable shape.

The collector 100 may further include a collection portion 130 and an extraction portion 140. Although depicted as two separate portions, the collection portion 130 and the extraction portion 140 may be the same portion of the collector 100.

The collection portion 130 includes an air inlet 132 and an outlet 134 for providing a path for an air stream to travel through the collector 100. Although depicted as having one inlet 132 and one outlet 134, the collection portion 130 may include any suitable number of inlets and outlets. The membrane structure 120 is positioned in the pathway of the air stream such that the air stream may travel through the membrane structure 120. As the air stream passes through the collection portion 130, materials contained within the airstream may be collected by the membrane structure 120.

The membrane structure 120 includes a porous substrate 122 and a mesoporous membrane 124 on the porous substrate 122. As described herein, the porous substrate 122 may be made of any suitable materials for supporting the mesoporous membrane, e.g., glass, silicon, metal, polymeric materials, or any other material that is reasonably strong and may be formed with reasonable tolerances. Further, the porous substrate may be manufactured using any suitable technique known in the art. For example the porous substrate may be manufactured using techniques described in U.S. Pat. No. 4,687,551 "Porous Films and Method of Forming Them."

The porous substrate 122 includes several pores that are of a size such that air passes through porous substrate 122. For example, the pore size of each pore may be greater than 1 mm. It may be preferred that the pore size may be greater than 5 mm. More preferably, the pore size may be greater than 10 mm. The substrate may be any suitable shape, e.g., rectilinear, circular, etc.

The mesoporous membrane 124 includes an active surface 126 and a support surface 128. The support surface 128 is placed on a major surface of the porous substrate 122 such that the substrate 122 supports the mesoporous membrane 124 and prevents it from tearing or rupturing. The mesoporous membrane 124 may be made from an inorganic material with a high elastic modulus, and is preferably modified to create a robust, reusable inorganic/organic hybrid membrane. It may be preferred that the mesoporous membrane 124 is a single layer alumina or silicon membrane. The mesoporous membrane 124 may be treated to facilitate extraction of a sample from the active surface 126 of the mesoporous membrane 124 as is further described herein.

The mesoporous membrane 124 may include several pores, where each pore has a selected pore size. The pore size may be any suitable size, e.g., 200 nm, 100, 20 nm, etc. Those skilled in the art will recognize that the pore size of the pores of the mesoporous membrane 124 may be selected based upon a particle size of the material to be sampled.

As air from inlet 132 passes through the membrane structure 120 and out air outlet 134, airborne biological organisms may collect on active surface 126 of mesoporous membrane 124, thereby providing sample 114 on active surface 126.

Once the sample 114 is collected on active surface 126 of the mesoporous membrane 124, the sample 114 is transferred to the extraction portion 140 of the collector 100. The sample 114 may be transferred using any suitable technique known in the art. For example, the membrane structure 120 may be rotated such that the sample 114 is transferred from the collection portion 130 to the extraction portion 140, e.g., by placing the membrane structure 120 on a rotating disc within the collector 100 (not shown). In an alternative embodiment, the membrane structure may be placed on a belt drive or platen such that the sample 114 is translated in a linear motion to the extraction portion 140.

An actuator 112 may be coupled to the membrane structure 120 such that the structure 120 is moved from the collection portion 130 to the extraction portion 140. Alternatively, the sample 114 may remain in the collection portion 130 of the collector 100 and be extracted from the membrane structure 120 without moving the sample 114 or the membrane structure 120.

Once transferred to the extraction portion 140 of collector 100, the sample 114 is extracted from active surface 126 of the mesoporous membrane 124. Any suitable technique for removing the sample 114 from the membrane structure 120 may be used, e.g., chemical, ultrasonic, electrostatic methods or a simple liquid wash. For example, extraction portion 140 may include a force transducer 146 that provides a force that removes the sample 114 from the membrane structure 120.

Figure 2:
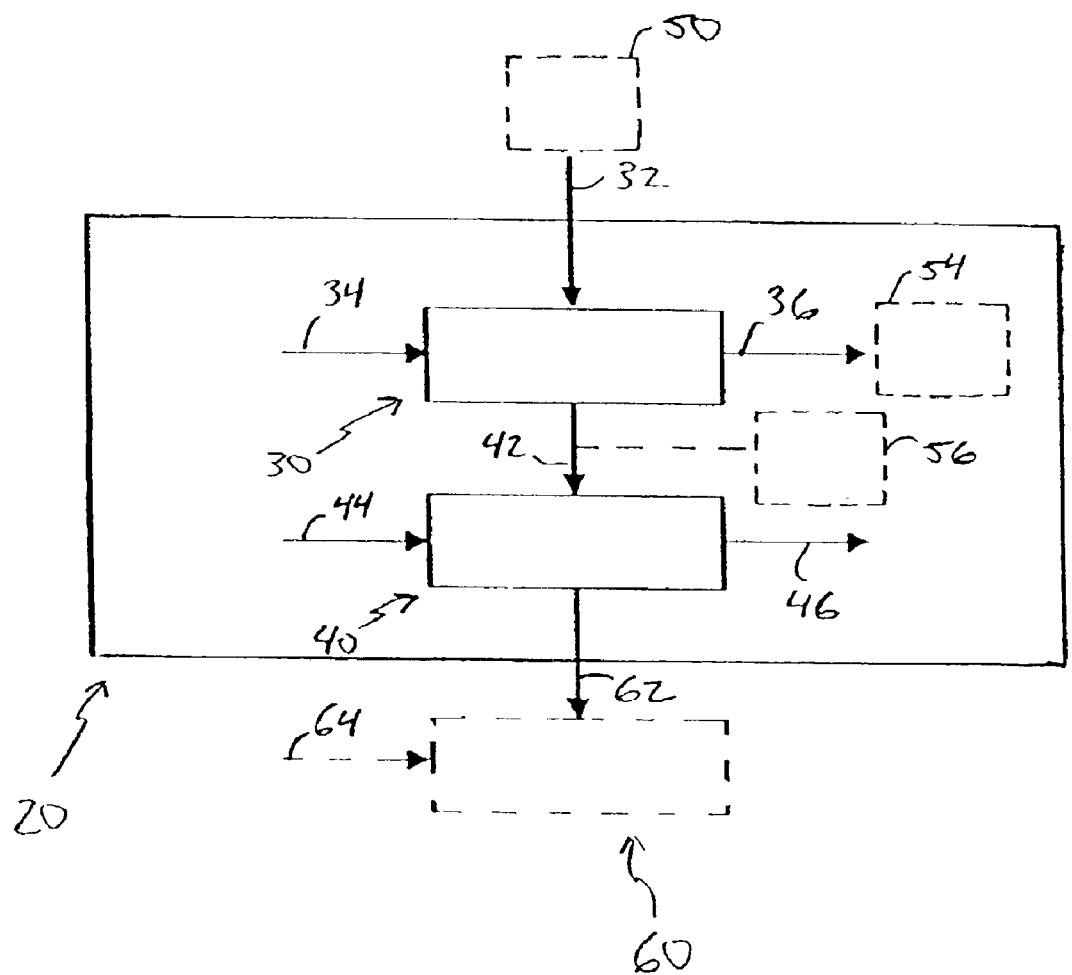
FIG. 2 is a schematic view of a system for detecting airborne biological organisms according to the present invention.

The extraction portion 140 of collector 100 may include an extraction inlet 142 and a sample outlet 144. The extraction inlet 142 may be utilized to provide various reagents that aid in the extraction of the sample 114 from the membrane structure 120. Such reagents are preferably aqueous (such as water or a buffer) if the mesoporous membrane 124 is hydrophilic, or relatively nonpolar (such as acetonitrile or DMSO) if membrane 124 is hydrophobic. Although depicted as having one extraction inlet, the extraction portion 140 may include any suitable number of extraction inlets. Once extracted, the sample 114 may be transferred from the extraction portion 140 of collector 100 into a detector (e.g., detector 30 of FIG. 2) via sample outlet 144.

Figure 3:
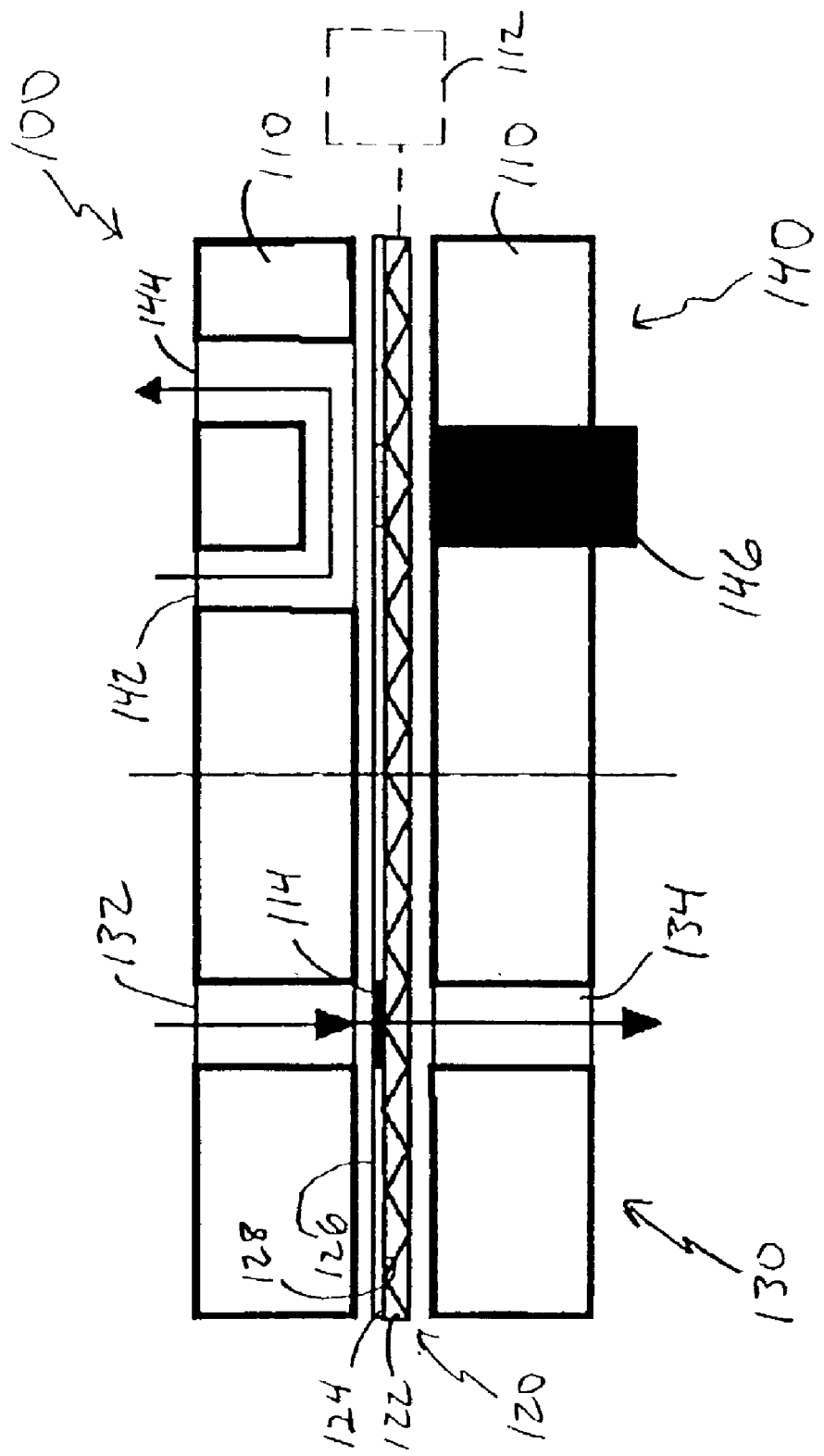
FIG. 3 is a schematic view of an illustrative embodiment of a collector using a membrane structure according to the present invention.
Figure 4:
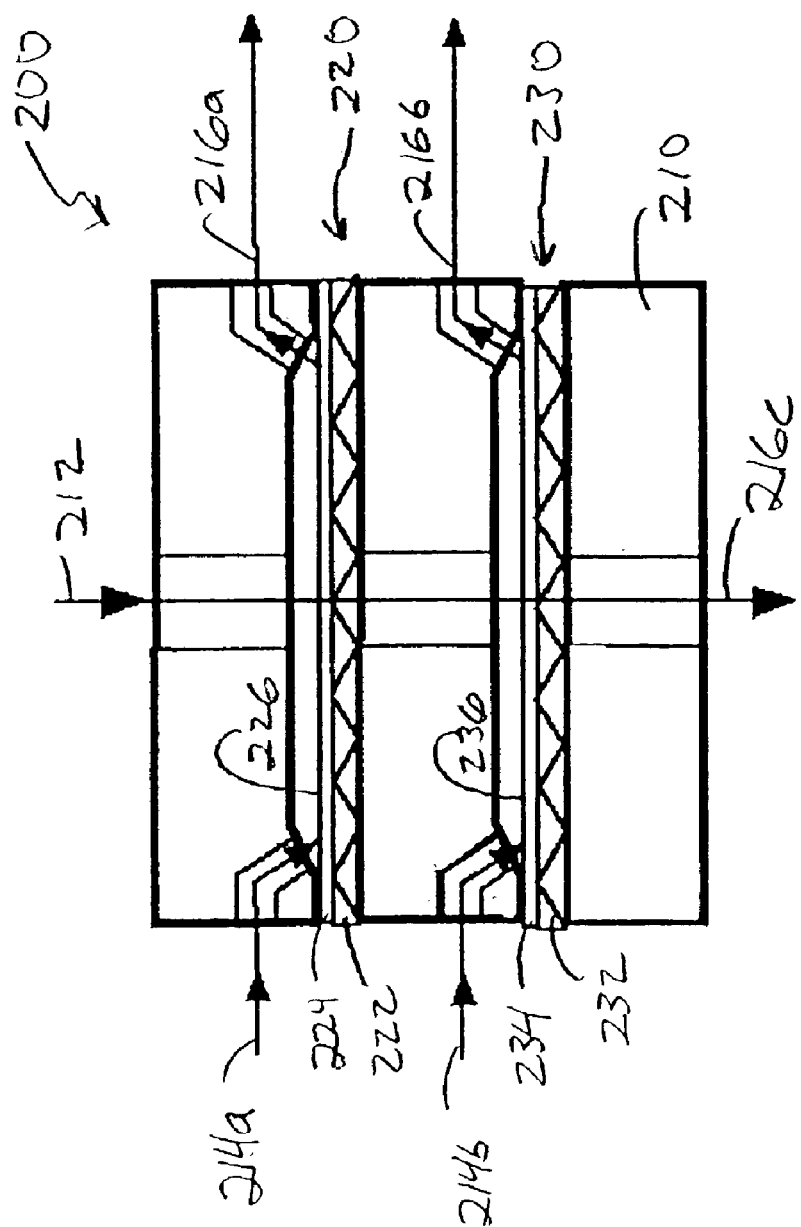
FIG. 4 is a schematic view of an illustrative embodiment of a separator using a first membrane structure and a second membrane structure according to the present invention.

FIG. 4 is a schematic diagram of a separator 200 according to another embodiment of the present invention. The separator 200 may be used with any system described herein (e.g., separator 40 of system 10 in FIG. 2). Separator 200 includes a body 210 and a sample inlet 212. The sample inlet 212 receives a sample from a collector (e.g., collector 100) or other source as described herein. Positioned within the body 210 of the separator 200 is a first membrane structure 220 and a second membrane structure 230. The membrane structures 220 and 230 are similar to other membrane structures described herein, e.g., membrane structure 120 of FIG. 3. For example, first membrane structure 220 includes a porous substrate 222 and a mesoporous membrane 224 on the porous substrate 222. The mesoporous membrane 224 includes several pores each having a first pore size. For example, the first pore size may be 200 nm or less.

The second membrane structure 230 may also include a porous substrate 232 and a mesoporous membrane 234 on the porous substrate 232. The mesoporous membrane 234 includes several pores each having a second pore size. The second pore size may be selected such that it isolates particles within the sample 314 that are of a different molecular weight than the molecular weight isolated by the first membrane structure 220. For example, if the first pore size is 200 nm, then the second pore size may be 100 nm.

Although depicted as having a first membrane structure 220 and a second membrane structure 230, the separator 200 may include any number of membrane structures, e.g., one or more. Each additional membrane structure may include the same or different pore sizes such that the various membrane structures isolate different molecular weights within the sample.

The separator 200 may also include a first reagent inlet 214a and a second reagent inlet 214b. The reagent inlets 214a and 214b are configured to receive reagents that may aid in separating samples as further described therein. The separator 200 may further include a first outlet 216a and a second outlet 216b. The outlets 216a and 216b are configured to provide a cross-flow of reagents over the surfaces of membrane structures 220 and 230.

The sample is received via inlet 212 from a collector (e.g., collector 100 of FIG. 3) and contacts an active surface 226 of the mesoporous membrane 224 of first membrane structure 220. A first reagent may be provided via first reagent inlet 214a to provide a cross-flow over active surface 226. Any suitable reagent may be used, e.g., water, buffer, surfactant, or organic solvent depending on the nature of the sample and the membranes. Particles of a size greater than the pore size of the mesoporous membrane 224 remain on active surface 226. The reagent removes these particles from active surface 226 of the first membrane structure 220 and carries the particles out of the separator through the first outlet 216a. These particles may then be transferred to a detector (e.g., detector 60 of FIG. 2) for detection and analysis as is known in the art.

Particles of a size such that they pass through the first membrane structure 220 then contact active surface 236 of second membrane structure 230. Reagents may then be introduced via second reagent inlet 214b as a cross-flow to extract particles from active surface 236 of second membrane structure 230 and out of the separator 200 via second outlet 216b. Any particles that pass through the second membrane structure 230 may then exit the separator 200 via third outlet 216c. The particles of the sample that exit the separator 200 either via the second outlet 216b and/or the third outlet 216c may then be transferred to a detector (e.g., detector 60 of FIG. 2) for detection and analysis as is known in the art.

EXAMPLES

The present invention is illustrated by the following examples. It is to be understood that the particular examples, materials, amounts, and procedures are to be interpreted broadly in accordance with the scope and spirit of the invention as set forth herein.

Example I

Physical Characterization of Alumina Membrane

Anodisc(® membranes from Fisher Scientific were evaluated, 13 mm diameter. The different sides (surfaces) of the membrane were called the active and the support sides, where the active side had smaller pore diameter sizes. The pore sizes and densities of 20 nm, 100 nm, and 200 nm nominal pore size membranes were determined using scanning electron microscope (SEM). SEM images provided detailed information about pore structure, such as pore size distribution, pore density, membrane structure, and membrane thickness.

Figure 5A:
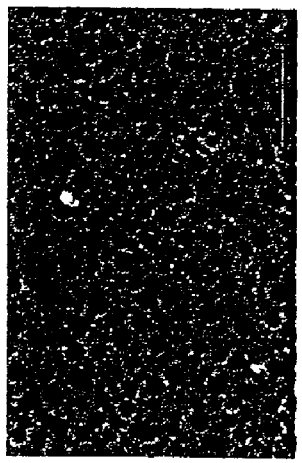
FIG. 5a is an image of an illustrative embodiment of a porous substrate of a membrane structure according to the present invention.
Figure 5B:
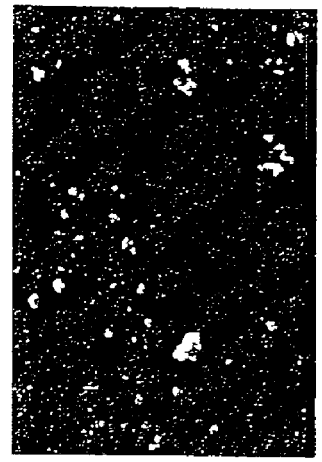
FIG. 5b is an image of an illustrative embodiment of a mesoporous membrane of a membrane structure according to the present invention.
Figure 5C:
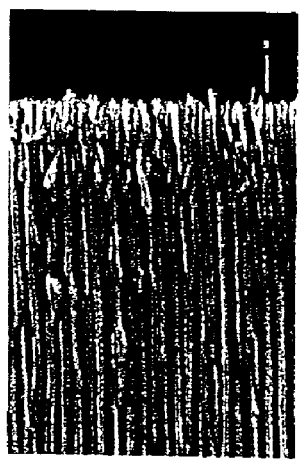
FIG. 5c is a cross-section image of the mesoporous membrane.

FIGS. 5a and 5b show the active and support side of a 20 nm nominal pore size membrane structure, respectively. The mean pore diameter on the active and support side of the mesoporous membrane was 23.1 nm and 189.0 nm, respectively. FIG. 5c is a cross sectional image of the membrane at the active surface. Clearly, the significant change in pore size and density between the active and supporting layers takes place in a very narrow region immediately adjacent to the surface. Table 2 summarizes the pertinent dimensions of a 20 nm nominal pore membrane.

TABLE 2

Pore dimensions

| Mean pore diameter (nm) | | Density (pores/m$^2$) | | Thickness (μm) | |
|---|---|---|---|---|---|
| Active | Support | Active | Support | Active | Support |
| 23.1 | 189 | 2.92 × 10$^{+14}$ | 8.06 × 10$^{+12}$ | 1.0 | 59.0 |

Example II

Synthesis of Hydrophilic Poly(Ethylene Glycol) (PEG)-Functionalized Mesoporous Alumina Membrane An inherent limitation in the application of membranes in all biological applications is the propensity of proteins to nonspecifically adsorb and foul the surface, which limits the application of almost all membrane technologies to a single use. Two chemical approaches were developed to form poly(ethylene glycol) (PEG) films on the membrane surface. Through these chemistries, specific proteins can be attached, and others can be prevent from adsorbing to the membrane.

Figure 6A:
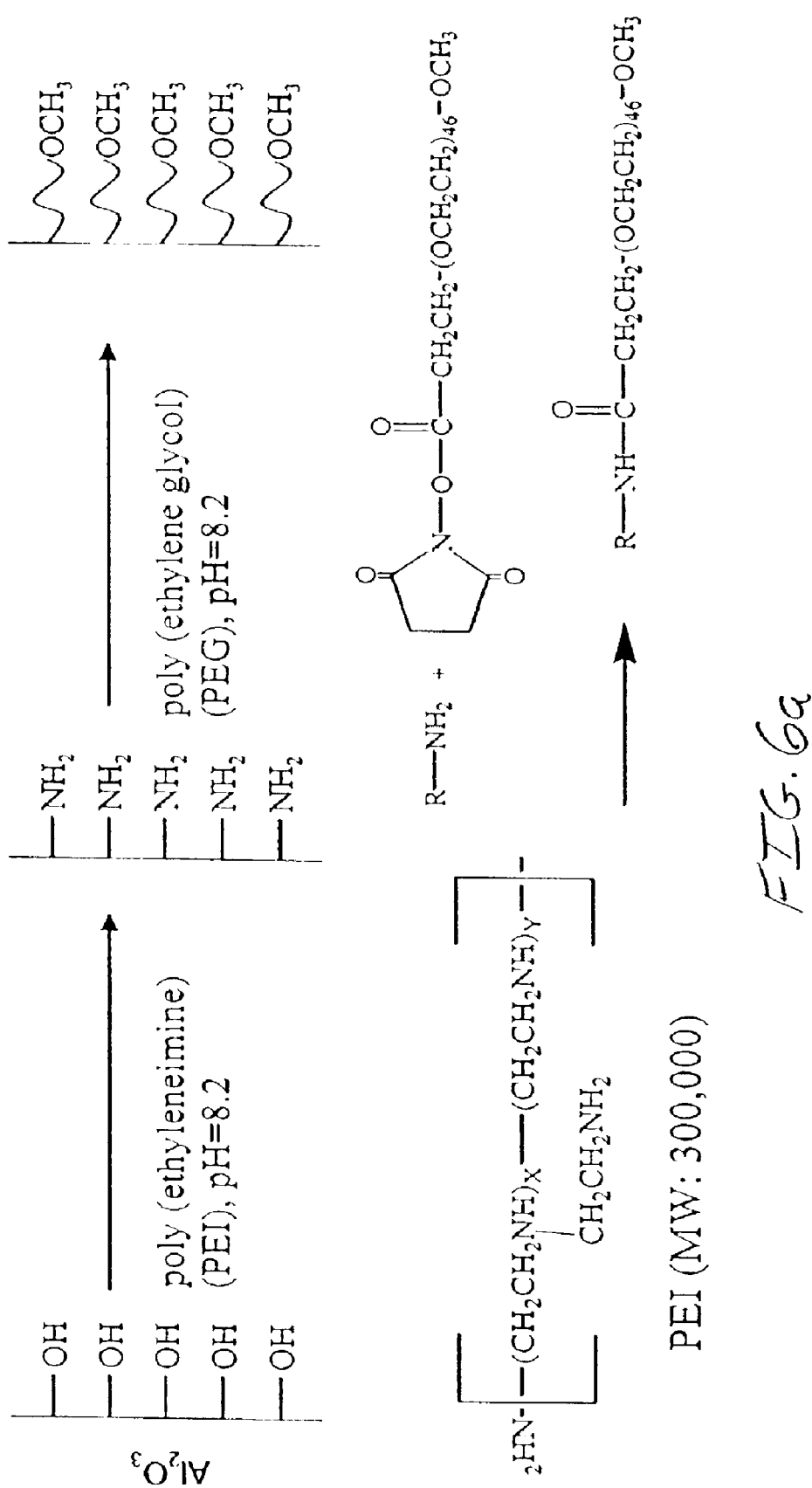
FIG. 6 shows three schemes for modification of alumina membranes using (a) high molecular weight poly (ethyleneimine) plus poly(ethylene glycol) (PEI-PEG); (b) formation of a self-assembled monolayer using a silane coupling reaction with PEG (silane-PEG); (c) (ω-methoxy terminated PEG) trimethoxysilane.
Figure 66:
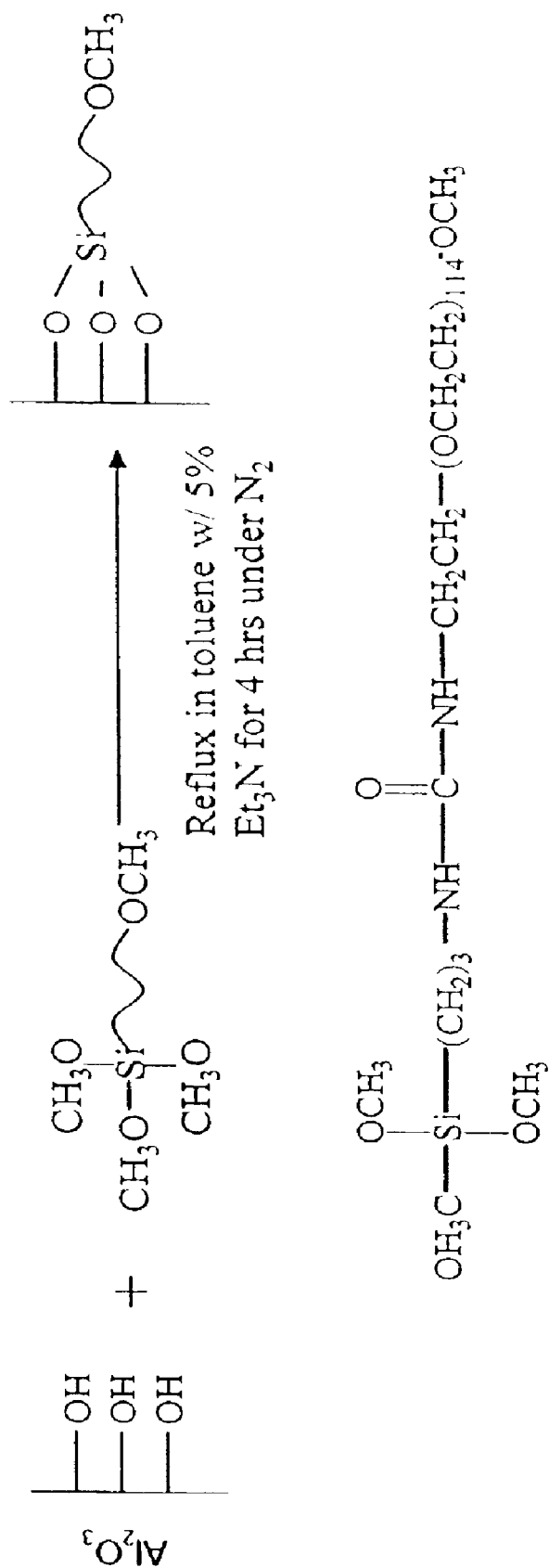
Figure 6C:
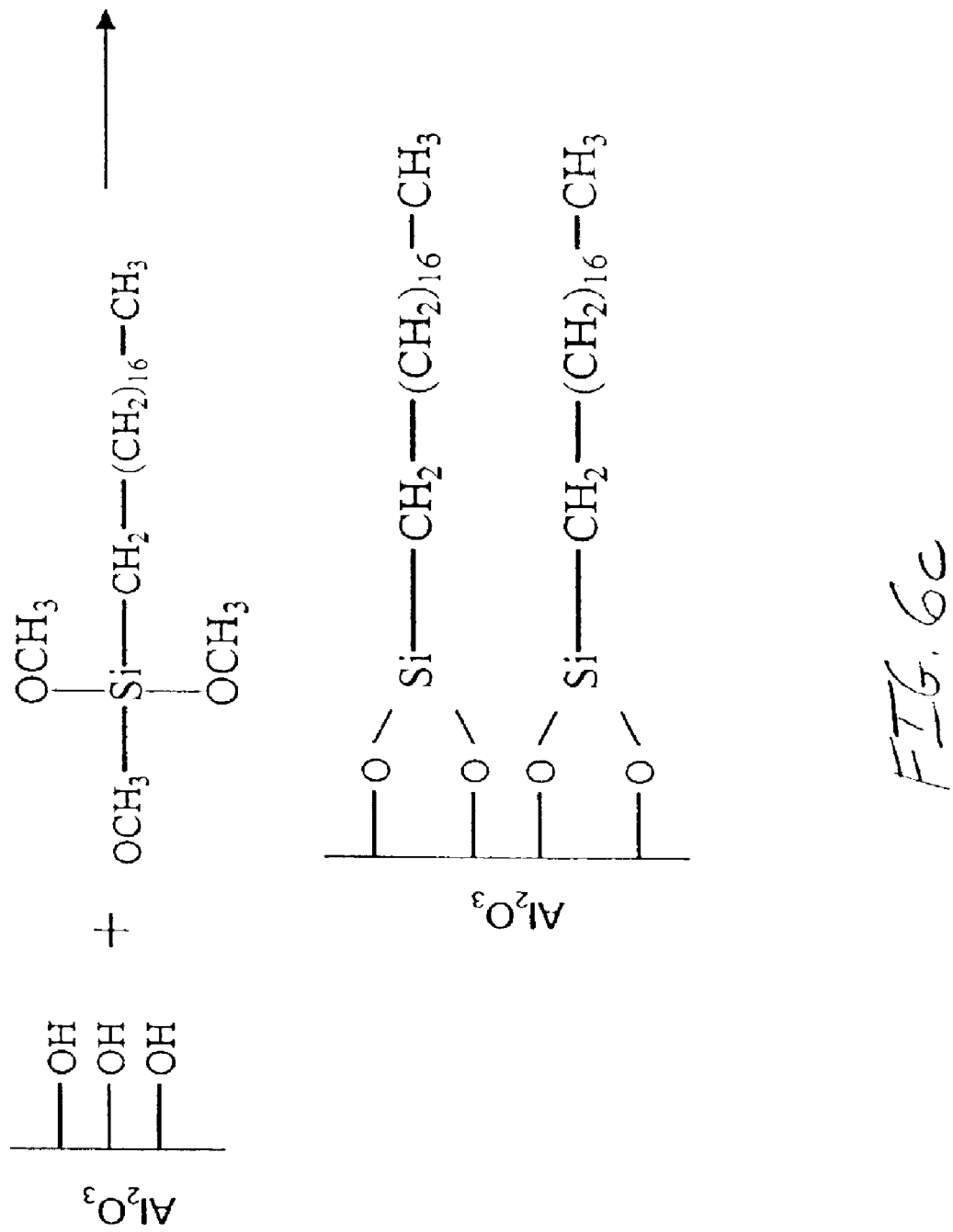

In this example, we describe the development and characterization of hydrophilic films on the alumina microporous membranes for collection and separation applications. Two chemical approaches for formation of PEG films on the membrane surface were investigated. The first method was based on a chemistry using a high molecular weight poly(ethyleneimine) (PEI), physically adsorbed on the membrane surface to provide functional groups to which N-hydroxysuccinimidyl methyl PEG propionic acid can be grafted (Metzger et al., *J. Vac. Sci. Technol. A.*, 17:2623 (1999)). The second method was based on the formation of a self-assembled monolayer (SAM) using a silane coupling reaction. (FIG. 6).

Materials

Anodisc® membranes from Fisher Scientific were evaluated, 13 mm diameter. Pore diameter sizes nominally rated at 20 nm. The pore geometry and the density of pore on the membrane surface were determined with scanning electron microscope (SEM). The different sides of the membrane were called the active and the support sides where the active side had smaller pore diameter sizes. The membranes were treated with ozone cleaner (UVO cleaner, model 42, Jetlight Co., Irvine Calif.) prior to the surface modification. N-hydroxysuccinimidyl (NHS) methoxy poly(ethylene glycol) propionic acid, MW 2000 (M-PEG) was purchased from Shearwater Corp (Huntsville, Ala.). (ω-methoxy terminated PEG) trimethoxysilanes (silane-PEG) with PEG MW 5000 was customer-synthesized from Shearwater Corp. Poly(ethyleneimine) (PEI) with a mean molecular weight of 300,000 was provided by BASF Chemicals (Polymin SNA, BASF, Rensselaer, N.Y.). Fraction V bovine serum albumin (BSA), grade VII albumin, chicken egg (ovalbumin), and fluorescence isothiocyanate (FITC) were obtained from Sigma (Sigma Chemical Company, St. Louis, Mo.).

Surface Chemistries (1) Poly(ethylene glycol) immobilization (FIG. 6a) was performed by reacting N-hydroxysuccinimidyl (NHS) ester PEGs with animated membrane surfaces that were prepared by a process of adsorption of PEI. PEI with a mean molecular weight of 300,000 was adsorbed on the surfaces by incubation with 5% (w/v) PEI in 50 mM Na$_2$CO$_3$, pH=8.2, for 2 hours. Excess PEI was removed by thoroughly rinsing in H$_2$O. All reactions were performed at room temperature unless otherwise stated, and Milli-Q (Millipore, Bedford, Mass.) water was used. PEG derivative was then reacted with the PEI surfaces in 50 mM Na$_2$CO$_3$, pH=8.2, for 2 hours at 37° C. The PEI-PEG-modified membranes were rinsed thoroughly in H$_2$O, dried and stored in N$_2$ atmosphere.

(2) A (ω-methoxy terminated PEG) trimethoxysilane (FIG. 6b) is reacted with the alumina membrane surface. 10 mg/ml of silane-PEG was prepared in anhydrous toluene and 5% of triethylamine was added as the catalyst. Membranes were placed in a reaction kettle and incubated with silane-PEG solution. After the solution was refluxed under N$_2$ atmosphere for 4 hours, the membranes were rinsed with toluene and refluxed another ½ hour to remove any ungrafted moieties on the surface. The silane-PEG modified membranes were then dried in a vacuum and stored under N$_2$.

Example III

Surface Characterization of PEG-Modified Mesoporous Alumina Membrane

Model System

PEI was deposited on an aluminum coated glass substrate, and PEG was grafted to it, modeling the PEG chemistry used to functionalize the mesoporous membrane (see Example II). Aluminum-coated glass was purchased from Thermospectra, Inc. The substrate was degreased in mixture of ethanol:dichloromethane:acetone (1:2:1 volume ratio), and then rinsed with acetone and distilled water. The surface was ozone cleaned for 10 minutes followed by immersing in the OTS solution (0.1% in toluene) for 30 minutes.

Ellipsometry was used to characterize the polymer coating on the aluminum-coated substrate. The thickness of PEI-only and PEI-PEG films were measured and are summarized in Table 3. The thickness of the PEI and PEI-PEG films suggests that conformal monolayers have been efficiently formed in both cases.

TABLE 3

Thicknesses

| Thickness of PEI (Å) | Thickness of PEG (Å) |
|---|---|
| 10 Å ± 1 Å | 40 Å ± 5 Å |

PEG-modified mesoporous alumina membranes

X-ray photoelectron spectroscopy (XPS) was used to characterize the surface of the PEG-modified membranes (Example II). XPS spectra probing the surface composition were taken before and after chemical modification of the membrane. XPS survey for the unmodified membrane indicated that there were ~10% residual carbon contaminants as well as Al and O from the surface composition of membrane. The spectra after PEI adsorption showed the appearance of N 1s peak and increasing intensity of C 1s which indicated the PEI adsorption on the membrane surface. PEI-PEG modified membrane showed the N 1s decreasing and C 1s increases due to the deposition of PEG on the membrane, as we expected.

XPS survey for silane-PEG films on the membrane also showed increasing of C 1s peak and appearance of Si 2p and N 1s peak, indicating the formation of a silane monolayer on the alumina membrane.

High-resolution spectra were collected of Al, Si, C, N and O on unmodified alumina membranes, PEI coated membranes, PEI-PEG coated membranes, and silane-PEG coated membranes. Analysis of the signal associated with each species allowed us to determine their relative amounts. This data is summarized in Table 4. The change in the relative amounts of chemical species associated with the membrane and specific chemicals allowed us to determine that a monolayer film of PEG was formed on the membranes with both chemistries.

Figure 7A:
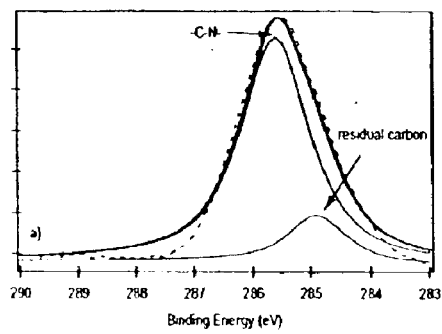
FIG. 7a is a high resolution spectra of C 1s for a PEI modified alumina membrane.
Figure 7B:
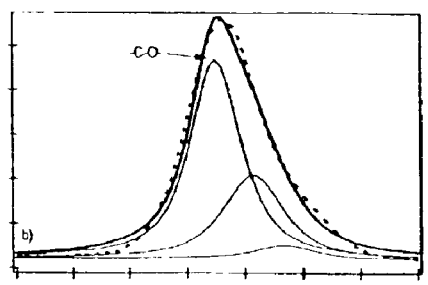
FIG. 7b is a high resolution spectra of C 1s for a PEI-PEG modified alumina membrane.
Figure 7C:
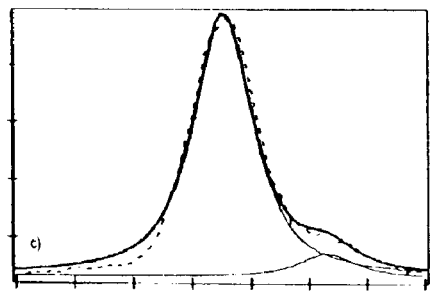
FIG. 7c is a high resolution spectra of C 1s for a silane-PEG modified alumina membrane.
Figure 8:
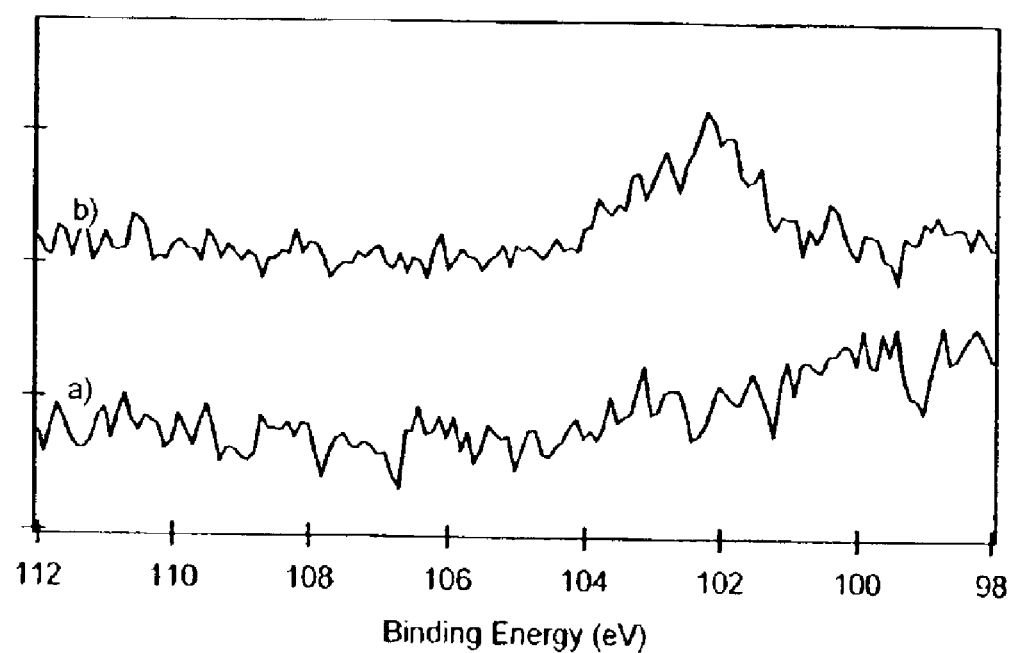
FIG. 8 is a high resolution spectra of Si 2p for a) unmodified and b)silane-PEG modified alumina membrane.

FIGS. 7a–7c show the high resolution of C 1s region for a) PEI (FIGS. 7a, b) PEI-PEG (FIGS. 7b, and c) silane-PEG modified membrane (FIG. 7c). Two different C 1s peaks were observed on the PEI modified membrane. The peak at 285.7 eV binding energy is associated with PEI. This result of XPS spectra of C 1s was consistent with previous work (See Beamson et al., *High Resolution XPS of Organic Polymers*, The Scienta ESCA300 Data Base, Wiley, N.Y. (1992)), which showed that adsorption of the branched high molecular weight PEI provided a thin film of irreversibly bound, amine groups on the membrane surface. The other peak at 284.9 eV binding energy is consistent with the saturated carbon, which may be attributed to either residual carbon or PEI.

layer of PEG grafted directly to the surface of the alumina surface. FIG. 8 shows a high resolution of Si 2p peak for an a) unmodified membrane and b) silane-PEG modified membrane. The observation of a silicon peak after silane-PEG reaction has been carried out on the membrane is consistent with the formation of a silane monolayer on the alumina membrane.

Example IV

Gas and Liquid Permeability of Mesoporous Alumina Membrane

The gas and liquid permeability of mesoporous alumina membranes was evaluated as a function of pore size. Anodisc® membranes from Whatman, Inc. having pore sizes of 20, 100 and 200 nm were tested. Slight variability between lots was noted, but reproducibility of experimental results using membranes from any single lot was high.

In addition, permeability measurements were made on 20 nm PEG-modified membranes (Example II) to determine if surface chemistries changed the functional behavior of the membrane. In other words, we wanted to determine whether chemical modification of the membrane surface influences the pore behavior.

Permeability, defined as flow rate per unit area per unit pressure, is the parameter used to characterize flow through porous materials. An instrument was designed and constructed to measure the flow of gases and liquids through a mesoporous membrane as a function of pressure. Of particular importance was the design of a membrane chamber for the measurement of the permeability of unsupported membranes. At low pressures, the permeability of the unsupported membrane was measured as a function of pressure. Conveniently, the rupture pressure for various mesoporous membranes supported by a substrate can be evaluated using the same instrument used to measure permeability.

Surprisingly, the permeability of these mesoporous membranes was higher than theoretical calculations would suggest. Moreover, although it was expected that as pore size increased, permeability would likewise increase, just the opposite was observed: as pore size increased, permeability

TABLE 4

|  | Binding energies | | | | | | | |
| --- | --- | --- | --- | --- | --- | --- | --- | --- |
| Chemistry | Al 2p 74.4 eV | Si 2p 102.0 eV | C 1s 249.9 eV | C 1s 285.7 eV | C 1s 286.5 eV | N 1s 398.6 eV | O 1s 530.3 eV | O 1s 532.0 eV |
| Unmodified membrane | 29.5% | — | 10.9% | — | — | — | 59.6% | — |
| PEI | 19.1% | — | 4.6% | 28.4% | — | 12.3% | 35.6% | — |
| PEI-PEG | 8.1% | — | 2.7% | 16.6% | 35% | 5.6% | 11% | 21% |
| Silane-PEG | 11.0% | 2.1% | 3.6% | — | 42.8% | 3.4% | 15.3% | 21.8% |

PEG modification resulted in the reduction of elemental components associated with the PEI modified membrane surface (N1s and Al 2p). The high resolution spectra of C 1s for PEG modified PEI membrane showed a decrease in the C 1s peak at 285.7 eV binding energy, which is a characteristic of PEI, and the appearance of a new type of carbon peak at 286.5 eV binding energy, indicating —C—O— associated with PEG. For silane-PEG, the dominant peak appeared at 286.5 eV binding energy, indicative of —C—O—. This spectrum is consistent with a dense monodecreased. These results, however, are consistent with those that would be predicted using slip-flow analysis, which is also surprising given the scale of the device. Table 5 shows experimental results (second column), theoretical results using slip flow prediction (third column) and theoretical results without slip flow prediction, i.e., permeability predicted for Hagen-Poiseuille flow (fourth column) for gas permeability of an unmodified membrane for use in the collector device of the invention.

TABLE 5

Gas permeability for unmodified alumina membrane

| Membrane Pore Size (nm) | Experimental Permeability (m/Pa s) | Slip Flow Prediction (m/Pa s) | Hagen-Poiseuille Flow Prediction (m/Pa s) |
|---|---|---|---|
| 20 | $1.90 \times 10^{-6}$ | $3.15 \times 10^{-6}$ | $5.09 \times 10^{-9}$ |
| 100 | $6.08 \times 10^{-6}$ | $6.31 \times 10^{-6}$ | $2.6 \times 10^{-7}$ |
| 200 | $6.88 \times 10^{-6}$ | $6.46 \times 10^{-6}$ | $5.3 \times 10^{-7}$ |

Table 6 illustrates liquid permeability and slip flow predictions for similar membrane pore sizes in an unmodified membrane for use in the separator device of the invention. Drag appears to be reduced compared to what would otherwise be expected, perhaps because the nanometer size of the pores may be on the same scale as the mean path length of the constituent molecules of the fluid and/or gas.

TABLE 6

Liquid permeability for unmodified alumina membrane

| Membrane Pore Size (nm) | Experimental Permeability (m/Pa s) | Slip Flow Prediction (m/Pa s) | Hagen-Poiseuille Flow Prediction (m/Pa s) |
|---|---|---|---|
| 20 | $2.67 \times 10^{-9}$ | $4.31 \times 10^{-9}$ | $9.12 \times 10^{-11}$ |
| 100 | $2.14 \times 10^{-8}$ | $1.21 \times 10^{-8}$ | $4.67 \times 10^{-9}$ |
| 200 | $2.18 \times 10^{-8}$ | $1.20 \times 10^{-8}$ | $1.0 \times 10^{-8}$ |

Table 7 compares gas and liquid permeability for 20 nm pore size unmodified membranes with permeability observed for otherwise identical PEG-modified membranes, as synthesized in Example II.

TABLE 7

Gas and liquid permeability for PEG-modified alumina membranes

| Membrane nominal pore size (nm) | Unmodified membrane (m/Pa s) | PEI-PEG membrane (m/Pa s) | Silane-PEG membrane (m/Pa s) |
|---|---|---|---|
| 20 nm ($N_2$) | $1.98 \times 10^{-06}$ | $7.08 \times 10^{-08}$ | $2.03 \times 10^{-06}$ |
| 20 nm ($H_2O$) | $7.00 \times 10^{-09}$ | 0 | $6.59 \times 10^{-09}$ |

The gas permeability for the PEI-PEG modified membranes decreased by at least two orders of magnitude compared with permeability for unmodified membrane. In liquid, the PEI-PEG membrane became effectively impermeable. This behavior is attributed to the deposition of PEI inside the pores and the swelling of the PEG on exposure to $H_{20}$. Although the PEI-PEG membrane chemistry may be suitable for some collector applications, it does not appear to be useful for separations (ultrafiltration).

It is important to note also that there is no significant decrease observed in permeability of the silane-PEG modified membrane compared with permeability for the unmodified membrane. The results of fluorescence microscopy (Example VI) and the permeability measurements for PEG-modified membranes demonstrated that silane-PEG modification minimizes nonspecific adsorption of proteins while maintaining high permeability. PEG-silane coated alumina membranes appear to be highly suitable for use in both collection and ultrafiltration of complex biological samples.

Gas Permeability as a Function of Relative Humidity

The gas permeability of a 200 nm nominal pore size unmodified membranes was measured as a function of relative humidity. This experiment simulated and evaluated the performance of the membrane as an airborne collector under what might be considered to be adverse environmental conditions. The permeability measurement apparatus was modified to allow the membrane permeability to be measured as a function of relative humidity.

Table 8 summarizes the permeability measurements as a function of relative humidity. Clearly, permeability of alumina membrane decreases as relative humidity increases; however, the change is very small. This result was an unexpected result as water is expected to condense in the nanometer size pores as the relative humidity increased. This unexpected result, which may be related to the straight pore geometry (FIG. 1) of the alumina membranes, indicates that these membranes are uniquely suited for aerosol collection.

TABLE 8

Permeability as a function of humidity

| Gas Content (RH/$H_2O$/air mole fraction) | Permeability (m/Pa · s) |
|---|---|
| Dry Air | $6.34 \times 10^{-6}$ |
| 36%/0.010 | $5.53 \times 10^{-6}$ |
| 64%/0.018 | $5.32 \times 10^{-6}$ |
| 97%/0.028 | $5.33 \times 10^{-6}$ |

Example V

Sample Collection and Extraction
Membrane Collector Efficiency

Figure 9B:
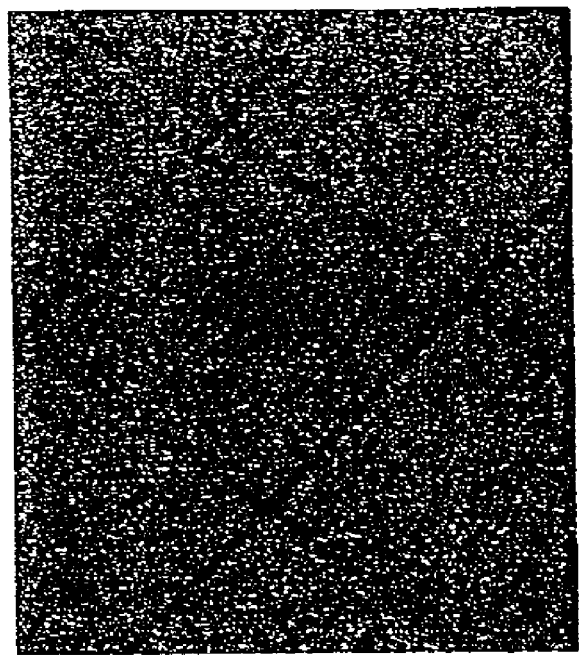
FIG. 9b is an image of the B. globigii spores solution of FIG. 19a after filtration.
Figure 9A:
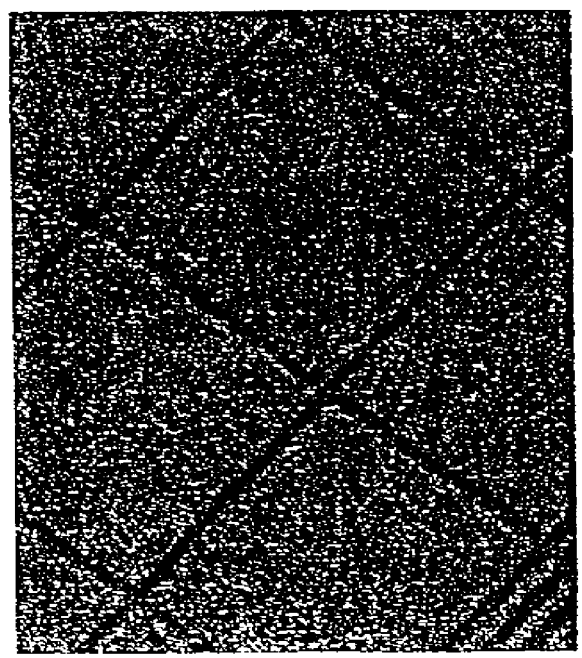
FIG. 9a is an image of B. globigii spores solution before filtration.
Figure 10A:
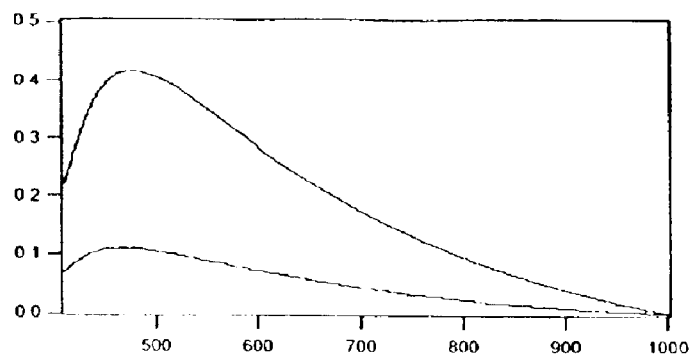
FIG. 10a is UV-spectra of B. globigii spores on a membrane before and after extraction using a 0.5% PBST rinse.
Figure 10B:
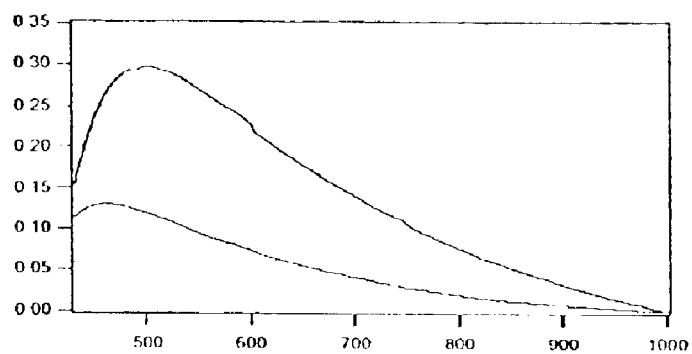
FIG. 10b is UV-spectra of B. globigii spores on a membrane before and after extraction using a 10% SDS rinse.
Figure 10C:
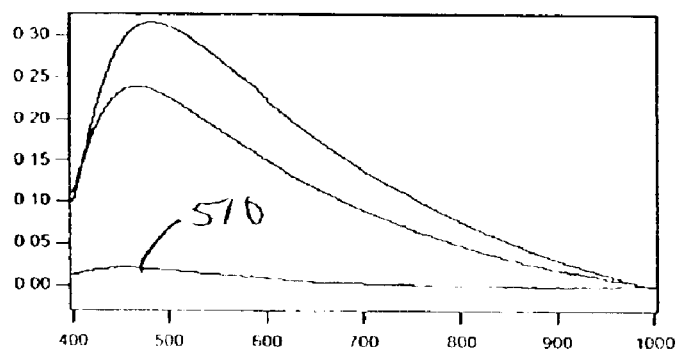
FIG. 10c is UV-spectra of B. globigii spores on a membrane before and after extraction using sonication.
Figure 11:
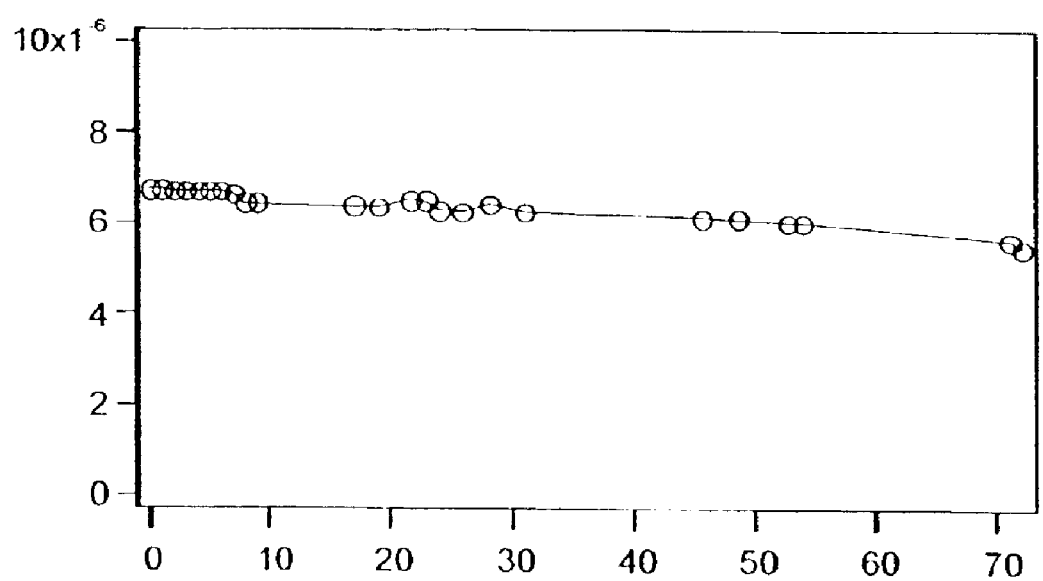
FIG. 11 plots permeability (m/Pa·s) versus time (hour) for a mesoporous membrane according to one embodiment of the present invention.
Figure 12A:
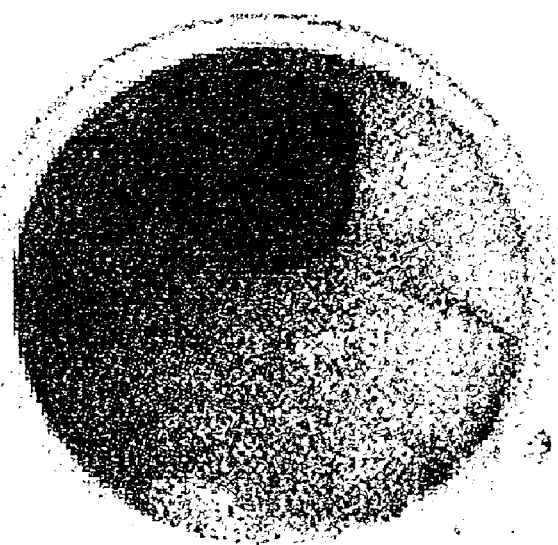
FIG. 12a is an image of protein binding to an unmodified membrane structure according to the present invention.
Figure 12B:
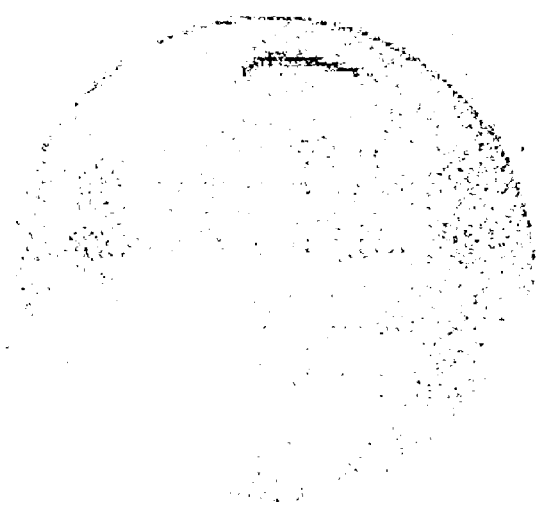
FIG. 12b is an image of protein binding to a PEG-modified membrane according to the present invention.
Figure 13:
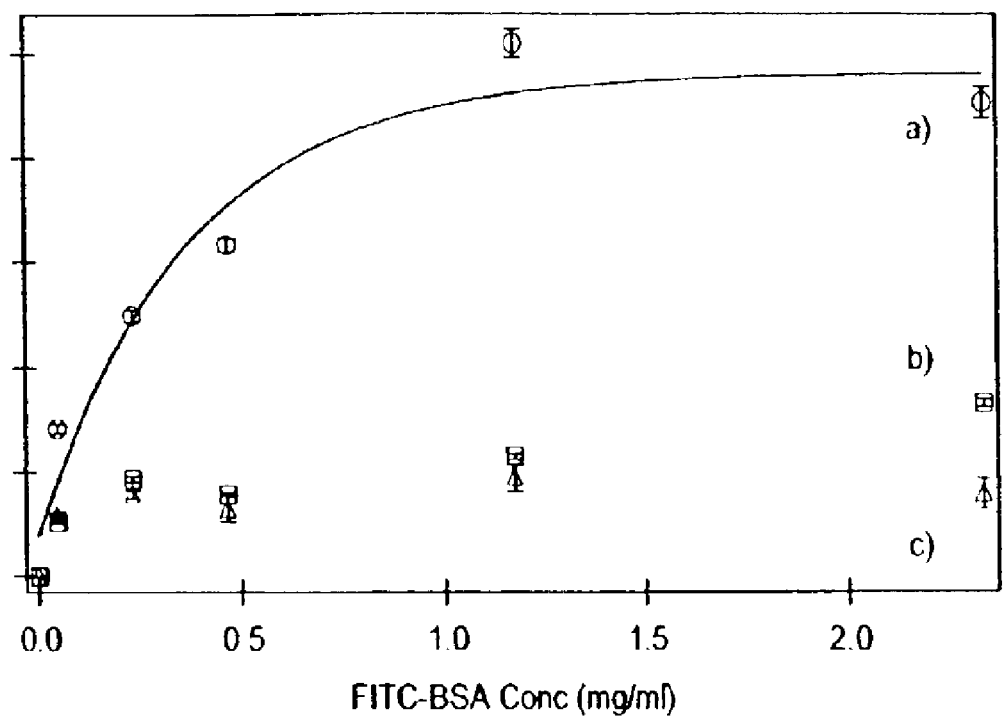
FIG. 13 plots fluorescence intensity of an unmodified (line and circles), silane-PEG (squares), and PEI-PEG modified alumina membrane (triangles).
Figure 14A:
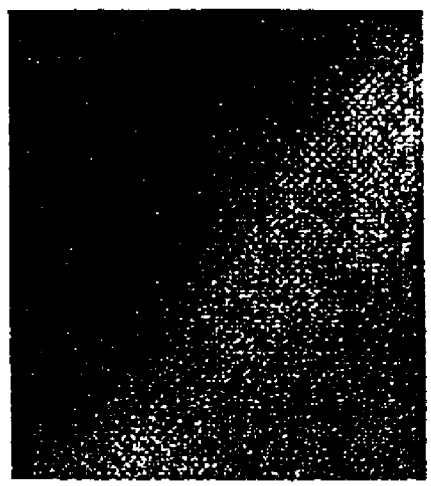
FIG. 14a is an image of one illustrative embodiment of an unmodified membrane structure according to the present invention.
Figure 14B:
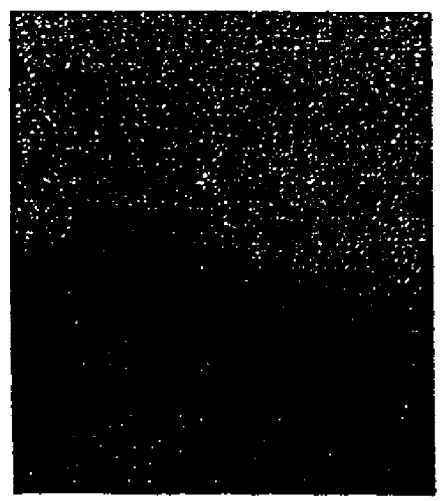
FIG. 14b is an image of the membrane structure of FIG. 14a, modified using PEG.

The performance of the membrane collector using an unmodified mesoporous membrane was evaluated for *B. globigii* liquid suspensions. The collection efficiency for *B. globigii* was determined using direct imaging. The 200 nm nominal pore membrane was sandwiched in a custom designed glass microanalysis filter holder assembly. The *B. globigii* spores solution was introduced, filtered, and collected. The number of spores was measured before and after filtration using hemocytometry. FIGS. 9a–9b show images of *B. globigii* spores solution before (FIG. 9a) and after filtration (FIG. 9b). The image after filtration clearly shows that there are no *B. globigii* spores in the solution. The results are summarized in Table 9. The collection efficiency of the 200 nm nominal pore size membranes for *B. globigii* is 100%.

TABLE 9

Spores in liquid suspension

| | Number of spores (spores/ml) |
|---|---|
| Before | $2 \times 10^8$ |
| After | None |

Determination of Recovery Efficiency

Continuous monitoring of the environment requires a thorough, rapid way to extract sample material that is trapped on the membrane surface. Typically this material forms a biofilm that, in other applications, has proven difficult to remove. Solvents and ultrasonic means of extraction were evaluated to determine the efficiency for removing *B. globigii* from the unmodified membrane surface. Phosphate buffered saline +Tween (PBST) 0.5% (a nonionic detergent) and SDS 10% (an ionic detergent) removed 75.4% and 76.4% of the spore material from the surface of the membrane, respectively. Rinsing with $H_2O$ only removed only 27% of the spores from the membrane surface. The membranes were also exposed to an ultrasonic energy source after wetting to determine if this technique could be used to remove *B. globigii* spores. UV-vis results indicate that more than 95% of the *B. globigii* spore material was removed from the membrane. These results are summarized in Table 10. Permeability measurements were performed after sonication and no significant change in permeability was observed, further confirming the membranes suitability for reuse applications.

TABLE 10

Removal efficiencies

| Methods | Removal Efficiency (%) |
|---|---|
| PBST 0.5% | 75.4 |
| SDS 10% | 76.4 |
| $H_2O$ | 26.9 |
| Sonication | 96.7 |

FIG. 10 shows the UV-Vis spectra of *B. globigii* spores on the membrane before and after extraction with a) PBST 0.5% (FIG. 10*a*), b) SDS 10% (FIG. 10*b*), c) $H_2O$ (FIG. 10*c*), and d) sonication (FIG. 10*c*, curve 510).

Environmental Air Sampling

The 200 nm nominal pore size unmodified membranes were used for atmospheric sampling to determine how long the mesoporous membrane would perform under real environmental conditions. Permeability measurements were carried out over a three day period during the month of July in the Midwestern U.S. with temperatures varying between 60–85 F., relative humidity varying between 30–95%, and a medium pollen count (see FIG. 11). It was surprising that membrane didn't clog for three full days for air sampling and the permeability only decreased by 15%.

Example VI

Inhibition of Protein Adsorption Onto PEG-Modified Alumina Membrane

The functional behavior of the PEI-PEG-modified membrane was characterized using enzymatic assay and fluorescence spectroscopy.

The efficiency of the PEG coating in inhibiting protein adsorption was first evaluated using a highly sensitive enzymatic assay. Specifically, various concentrations of the enzyme horseradish peroxidase (HRP) were added to the membrane described in Example II and allowed to dry. The membrane was subsequently washed with water and exposed to reagents that produce an intense blue color in the presence of HRP.

FIG. 12 shows the results of an assay in which unmodified and PEG-modified membranes were exposed to 10 μg/ml of HRP. The blue spot where the HRP was added to the unmodified membrane is clearly visible to naked eye, while no spot is visible on PEG modified mesoporous membrane surface.

Functional Behavior of PEG Films on the Membranes

For more quantitative measurement, fluorescence spectroscopy was used. Bovine serum albumin (BSA) was labeled with fluorescence isothiocyanate (FITC). The membranes were soaked in FITC-BSA solution for an hour and rinsed with phosphate buffer (pH=7.2). FIG. 13 shows the fluorescence intensity as a function of FITC-BSA concentration added to the membrane. Fluorescence intensity increased to saturation on the unmodified surface as FITC-BSA concentration increased to 2 mg/ml, however fluorescence intensity hardly increased with increasing FITC-BSA increased concentration on the modified surface. BSA adsorption on the unmodified membranes follows a Langmuir-type isotherm typically observed for proteins. The PEG coated membranes clearly adsorbed significantly less protein than the unmodified membrane. These results demonstrate that the PEG-modified films on the membranes inhibit non-specific protein binding.

FIG. 14 shows CCD images of unmodified (FIG. 14*a*) and modified with PEI-PEG coating (FIG. 14*b*) with FITC-BSA. These images were acquired at the edge of the mesoporous membrane as indicated by the black area where no protein was adsorbed.

These results clearly show that a PEG coating on the membranes inhibits protein adsorption, probably by minimizing multivalent interaction between the protein and the substrate surface.

Example VII

Protein Diffusion Through PEG-Modified Mesoporous Alumina Membrane

Protein diffusion experiments were conducted to investigate how biological molecules interact with the PEG modified membrane. A diffusion cell was designed and constructed for determination of protein diffusivity through the membrane. For these experiments, ovalbumin (OA) was chosen as a model protein because it is well characterized. OA molecules disperse in the monomeric state at a low concentration and can be considered to be a rigid sphere with a radius of 25 Å. See Matsumoto et al., *Journal of Colloid and Interface Science*, 160:105 (1993). The effective diffusion coefficient of ovalbumin molecules through membrane was determined experimentally and compared with a theoretical value.

Theoretical diffusivity for OA molecules through the membrane was calculated using a two-layer membrane model. That is, the membrane is modeled as 2 layers of thickness $l_1$ and $l_2$ in which OA diffuses as $D_1$ and $D_2$, where 1 and 2 denote for active and support side, respectively. The resistance to diffusion of the whole membrane is simply the sum of the resistances of each component, assuming that there are no barriers to diffusion between them. See J. Crank, *The Mathematics of Diffusion*, Oxford Press (1956).

$$\frac{l_1 + l_2}{D_{eff}} = \frac{l_1}{D_1} + \frac{l_2}{D_2}$$

A mathematical model for the protein diffusion can be derived in terms of Fick's law and the mass balance (see Dalvie et al., *Journal of Membrane Science*, 71:247 (1992) that provides a relationship for the OA concentration in the low concentration cell, sink, $C_L(t)$:

$$\frac{C_L}{C_0} = \frac{V_H}{V_L + V_H}\left[1 - \exp\left(\frac{-n\pi r^2 K_m (V_L + V_H)t}{V_L V_H}\right)\right]$$

where $C_O$ is the initial concentration of OA in reservoir; $V_H$ and $V_L$ are the volumes of reservoir and sink, respectively; n is the number of pores in effective diffusion area; r is the effective pore radius; and $K_m$ is the effective mass transfer coefficient. The concentration of OA in sink can be mea sured as a function of time to determine the effective OA diffusivity, $$D_{\textit{eff}}\left(K_m = \frac{D_{\textit{eff}}}{l}\right).$$

The theoretical value of the diffusivity calculated from the membrane (20 nm pore size) and protein properties and the measured diffusivities are summarized in Table 11. The diffusivity measured through the unmodified membrane is in excellent agreement with the diffusivity calculated from the membrane and protein properties. A diffusivity could not be measured for ovalbumin across the PEI-PEG membrane, which is consistent with our model of plugged pores. Surprisingly, the diffusivity of ovalbumin across the silane-PEG membrane exceeded that of the bare membrane. These are initial results that need to be confirmed, but if they are correct they would indicate that the silane PEG actually increases the diffusivity of OA across the membrane.

TABLE 11

| | Diffusivity | | |
|---|---|---|---|
| Theoretical Value (cm$^2$/s) | Unmodified | PEI-PEG | Silane-PEG |
| 6.37 × 10$^{-7}$ | 8.19 × 10$^{-7}$ | 0 | 7.54 × 10$^{-7}$ |

Example VIII

Synthesis of Hydrophobic n-Octadecyl Trichlorosilane (OTS)-Functionalized Mesoporous Alumina Membrane A hydrophobic membrane surface was made by depositing n-octadecyl trichlorosilane (OTS) on an aluminum coated glass substrate, modeling a hydrophobic chemistry that could be used to functionalize alumina mesoporous membranes. Aluminum-coated glass was purchased from Thermospectra, Inc. The substrate was degreased in mixture of ethanol:dichloromethane:acetone (1:2:1 volume ratio), and then rinsed with acetone and distilled water. The surface was ozone cleaned for 10 minutes followed by immersing in the OTS solution (0.1% in toluene) for 30 minutes.

Contact angle measurement was performed to investigate the surface chemistries on the aluminum coated glass substrate. The contact angles of these surfaces are summarized in Table 12, and the high contact angle of the OTS coated surface suggest that a monolayer of OTS has been successfully formed.

TABLE 12

| | Contact angles | |
|---|---|---|
| Degreased | Ozone Cleaned | OTS coated |
| 51.7° ± 2.1° | 10.5° ± 2.1° | 88.0° ± 1.4° |

The complete disclosures of all patents, patent applications including provisional patent applications, publications, and electronically available material cited herein are incorporated by reference. The foregoing description and examples have been provided for clarity of understanding only. It is to be understood that the particular examples, materials, amounts, and procedures are to be interpreted broadly in accordance with the scope and spirit of the invention as set forth herein. No unnecessary limitations are to be understood therefrom. The invention is not limited to the exact details shown and described; many variations will be apparent to one skilled in the art and are intended to be included within the invention defined by the claims.

What is claimed is:

1. A collector for collecting a biological material present in a gaseous sample, the collector comprising a collection portion comprising:
   a membrane structure providing a non-tortuous flow path therethrough comprising a mesoporous membrane composed of an inorganic material having an active surface an opposite support surface, and a porous substrate adjacent the support surface; and at least one inlet and outlet providing a path for the flow of a gas through the membrane structure;
   wherein the membrane structure is pretreated with an organic material selected to collect biological material from a gaseous sample on the active surface of the mesoporous membrane, said collector further comprising an extraction portion adjacent to said collection portion capable of being in fluid communication with the membrane structure containing the removed biological material.

2. The collector of claim 1 further comprising an actuator for moving the membrane structure from the collection portion to the extraction portion.

3. The collector of claim 1 wherein the mesoporous membrane comprises pores having a diameter of at least about 200 nm.

4. The collector of claim 1 wherein the at least one membrane structure comprises first and second membrane structures, said first and second membrane structures comprising mesoporous membranes having different pore sizes.

5. The collector of claim 1 wherein the mesoporous membrane exhibits a gas permeability of between about 1.90×10$^{-6}$ and about 2.67×10$^{-9}$ (m/Pa s).

6. The collector of claim 1 wherein the mesoporous membrane comprises pores extending therethrough perpendicular to the active surface.

7. The collector of claim 1 wherein the mesoporous membrane is derivatized with an organic material.

8. A system for detecting a biological material present in a gaseous sample, the system comprising:
   a collector comprising (i) a collector portion comprising a membrane structure including a mesoporous membrane composed of an inorganic material having an active surface and opposite support surface, and a porous substrate adjacent the support surface, at least one inlet and outlet providing a path for the flow of a gas through the membrane structure, wherein the collector is operable to collect the biological materials on the active surface of the mesoporous membrane; and (ii) an extraction portion in fluid communication with the membrane structure, wherein the extraction portion adjacent to said collector portion is operable to remove the biological materials from the active surface of the mesoporous membrane; and
   a separator in fluid communication with the collector, wherein the separator comprises at least one membrane structure comprising a mesoporous membrane comprising an inorganic material, the membrane having an active surface and a support surface, and a porous substrate adjacent the support surface of the mesoporous membrane; and at least one inlet and outlet providing a path for the flow of a liquid through the at least one membrane structure;

wherein the collector is configured to provide a liquid sample comprising the extracted biological materials to the separator, and further wherein the separator is operable to receive the liquid sample from the collector and separate the biological materials in the liquid sample.

9. The system of claim 8 further comprising a detector in fluid communication with the separator, wherein the detector is configured to receive the separated biological materials from the separator, and wherein the detector is operable to detect and analyze the separated biological materials.

10. The system of claim 8 wherein the active surface of the mesoporous membrane of at least one of the collector or the separator comprises an organic material.

11. The system of claim 8 wherein the collector further comprises an actuator for moving the membrane structure from the collection portion to the extraction portion.

12. The system of claim 8 wherein the extraction portion of the collector comprises a transducer operable to extract the biological materials from the active surface of the mesoporous membrane.

* * * * *